US007169382B2

(12) United States Patent
Chopart et al.

(10) Patent No.: US 7,169,382 B2
(45) Date of Patent: Jan. 30, 2007

(54) RECONSTRUCTED EPIDERMIS/SKIN EQUIVALENT COMPRISING A CERAMIDE 7 AND /OR 5.5 AND LIPID LAMELLAR VESICULAR COMPOSITIONS COMPRISING CERAMIDE 7 AND/OR 5.5 COMPOUNDS

(75) Inventors: Mélanie Chopart, Paris (FR); Isabelle Castiel, Nice (FR); Jean-Thierry Simonnet, Cachan (FR)

(73) Assignee: L'Oreal, Paris (FR)

( * ) Notice: Subject to any disclaimer, the term of this patent is extended or adjusted under 35 U.S.C. 154(b) by 451 days.

(21) Appl. No.: 10/766,016

(22) Filed: Jan. 29, 2004

(65) Prior Publication Data

US 2004/0248294 A1  Dec. 9, 2004

Related U.S. Application Data

(60) Provisional application No. 60/477,049, filed on Jun. 10, 2003, provisional application No. 60/477,053, filed on Jun. 10, 2003.

(30) Foreign Application Priority Data

Jan. 30, 2003  (FR) .................................. 03 01058
Jan. 30, 2003  (FR) .................................. 03 01059

(51) Int. Cl.
*A61K 7/48* (2006.01)
*A61K 7/00* (2006.01)
*A61K 47/22* (2006.01)
*A61K 45/00* (2006.01)
*C12N 5/08* (2006.01)

(52) U.S. Cl. .................. 424/78.03; 424/401; 424/450; 424/886; 435/371; 514/474; 514/943

(58) Field of Classification Search ............. 424/78.03, 424/401, 450, 886; 435/371; 514/474, 943
See application file for complete search history.

(56) References Cited

U.S. PATENT DOCUMENTS

| 5,149,860 | A | 9/1992 | Zysman et al. |
| 5,198,470 | A | 3/1993 | Zysman et al. |
| 5,741,518 | A | 4/1998 | Ribier et al. |
| 5,861,153 | A | 1/1999 | Schmidt et al. |
| 5,866,158 | A | 2/1999 | Ribier et al. |
| 5,869,034 | A * | 2/1999 | Montastier et al. ...... 424/78.03 |
| 5,925,364 | A * | 7/1999 | Ribier et al. ................. 424/401 |
| 6,596,695 | B2 * | 7/2003 | Castiel et al. .................. 514/27 |
| 6,605,466 | B1 | 8/2003 | Pageon et al. |
| 6,660,522 | B2 | 12/2003 | Pageon et al. |
| 6,846,675 | B2 * | 1/2005 | Conrad et al. .............. 435/371 |
| 6,890,754 | B2 * | 5/2005 | Pageon et al. .............. 435/371 |
| 2002/0042380 | A1 | 4/2002 | Castiel et al. |
| 2003/0176366 | A1 | 9/2003 | Castiel et al. |

FOREIGN PATENT DOCUMENTS

| EP | 0 582 503 A1 | 2/1994 |
| FR | 2 807 320 A1 | 10/2001 |
| FR | 2 811 556 A1 | 1/2002 |
| JP | 2000 143598 A | 5/2000 |

OTHER PUBLICATIONS

Robson et al., "6-Hydroxy-4-Sphingenine in Human Epidermal Ceramides", Journal of Lipid Research, vol. 35, 1994 pp. 2060-2068.
Dreher et al., "Comparison of Cutaneous Bioavailability of Cosmetic Preparations Containing Caffeien or α-Tocopherol Applied on Human Skin Models or Human Skin ex vivo at Finite Doses", Skin Pharmacology and Skin Applied Physiology, vol. 15, No. Suppl. 1, 2002 pp. 40-58.
Castiel-Higounenc et al., "Augmentation du Contenu en Céramides des Épidermes Humains Reconstruits Apreés Traitement Avec un Sphingolipide Exogène À Base Sphinganine", Les Nouvelles Dermatologiques, vol. 18, No. 8, 1999 pp. 541-546.
French Search Report Corresponding to FR 03/01058 Issued on Nov. 4, 2003, 2 Pages.
French Search Report Corresponding to FR 03/01059 Issued on Dec. 17, 2003, 2 Pages.

* cited by examiner

*Primary Examiner*—Herbert J. Lilling
(74) *Attorney, Agent, or Firm*—Buchanan Ingersoll & Rooney PC

(57) ABSTRACT

A reconstructed epidermis/skin equivalent supplemented with at least one ceramide 7 and/or 5.5 compound, suited for reinforcing the barrier function of normal human epidermis and for improving the barrier function of dry skin and of reconstructed skin or skin equivalents, is prepared by introducing the at least one ceramide 7 and/or 5.5 compound into the culture medium of such reconstructed epidermis/skin equivalent and/or topically applying onto the face surface of such reconstructed epidermis/skin equivalent a composition which comprises lipid lamellar vesicles incorporating at least one ceramide 7 and/or 5.5 compound.

43 Claims, 2 Drawing Sheets

Figure 1:
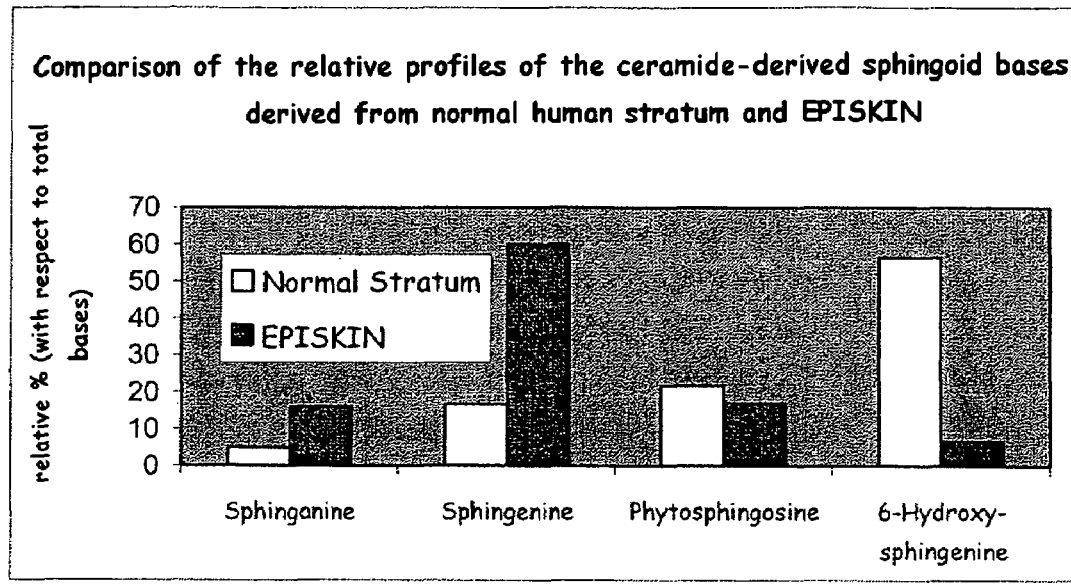

* : Results significant at 15 %

RECONSTRUCTED EPIDERMIS/SKIN EQUIVALENT COMPRISING A CERAMIDE 7 AND /OR 5.5 AND LIPID LAMELLAR VESICULAR COMPOSITIONS COMPRISING CERAMIDE 7 AND/OR 5.5 COMPOUNDS

CROSS-REFERENCE TO PRIORITY/PROVISIONAL APPLICATIONS

This application claims priority under 35 U.S.C. § 119 of FR 03/01058 and FR 03/01059, both filed Jan. 30, 2003, and of provisional application Ser. Nos. 60/477,049 and 60/477,053, both filed Jun. 10, 2003, each hereby expressly incorporated by reference and each assigned to the assignee hereof. This application is also a continuation of said '049 and '053 provisionals.

BACKGROUND OF THE INVENTION

1. Technical Field of the Invention

The present invention relates to a method for preparing a reconstructed epidermis or a skin equivalent supplemented with at least one derivative of ceramide 7 and/or 5.5, comprising introducing at least one derivative of ceramide 7 and/or 5.5 into the culture medium for said reconstructed epidermis or said skin equivalent and/or in topically applying to said reconstructed epidermis or said skin equivalent a composition based on lipid lamellar vesicles incorporating at least one derivative of the ceramide 7 and/or 5.5 family.

The invention also relates to a reconstructed epidermis or a skin equivalent containing at least one derivative of the ceramide 5.5 family.

The present invention also relates to a composition comprising a dispersion, in an external aqueous phase, of vesicles formed by lipid lamellar phases separated from one another by hydrophilic layers, said lamellar phases comprising at least one amphiphilic lipid, and at least one derivative of the ceramide 7 and/or ceramide 5.5 family included in said lipid lamellar phases, and also to the use of said composition for reinforcing the barrier function of normal human epidermis, and improving the barrier function of an epidermis exhibiting even a slight deficiency in 6-hydroxy-4-sphingenine-base ceramides, in particular of dry skin and of reconstructed skin or skin equivalents.

2. Description of Background and/or Related and/or Prior Art

Human skin consists of two compartments, namely a deep compartment, the dermis, and a superficial compartment, the epidermis. The epidermis is in contact with the outside environment. Its role consists in protecting the organism against dehydration and outside attacks, whether they are chemical, mechanical, physical or infectious.

The natural human epidermis is composed mainly of three types of cells, which are keratinocytes, present in great majority, melanocytes and Langerhans cells. Each of these cell types contributes by virtue of its own functions to the essential role played in the organism by the skin.

The cells constituting the epidermis are delimited by a lipid domain. During differentiation, the phospholipids, the role of which consists in developing the fluid structure of the cell membranes of the living layers of the epidermis, are gradually replaced with a mixture composed mainly of fatty acids, cholesterol and sphingolipids.

These lipids are organized in specific lamellar liquid crystal phases, the integrity of which depends not only on the quality of the fractions present but also on their respective proportions. This lamellar structure of the lipids of the lipid domain of the epidermis is responsible for the epidermal barrier function.

Epidermal lipids are synthesized mainly in the living epidermis. They consist mainly of phospholipids, ceramides (or sphingolipids), cholesterol, free fatty acids, triglycerides, cholesterol esters and alkanes.

Ceramides are one of the essential constituents of epidermal lipids, making it possible, partly, to provide the lamellar liquid crystal structure thereof, but also the barrier function of the epidermis.

Ceramides are made up of a sphingoid base, which may be of four types, sphinganine, sphingenine, phytosphingosine and 6-hydroxy-4-sphingenine, and of a fatty acid which may be saturated, $\alpha$-hydroxylated or $\omega$-esterified. The various possible combinations between bases and fatty acids result in about ten ceramides listed by Robson, K. J.; Stewart, M. E.; Michelsen, S.; Lazo, N. D.; Downing, D. T., "6-hydroxy-4-sphingenine in human epidermal ceramides," in *J. Lipid Res.*, 1994, 35:2060–2068; and Chopart M., Castiel-Higounenc I., Arbey E., Guey C., Gaetani Q., Schmidt R., "The Normal Human stratum corneum: a new ceramide profile," Perspectives in Percutaneous Penetration, 8th International Conference, Antibes Juan-Les-Pins—France, Apr. 2–6, 2002.

It has been possible to develop models which are more or less close to human skin. Mention may, for example, be made of the models described in EP-A-285471, EP-A-285474, EP-A-789074, EP-A-502172, EP-A-418035, WO-A-9116010, EP-A-197090, EP-A-20753, FR-A-2665175, FR-A-2689904 and FR-A-2792650.

Very generally, the models of reconstructed skin described in those documents comprise human keratinocytes possibly combined with other skin cells such as melanocytes and/or Langerhans cells, deposited on a support, often a dermis equivalent, and cultured under conditions such that they enter into a program of differentiation resulting in the formation of an epidermis equivalent. The dermis equivalents described to date are either artificial membranes, such as, for example, filters of the Millipore trademark, subcutaneous substitutes based on collagen, plastic or any other support compatible with cell viability, or supports which are more developed in order to make them closer to natural dermis, such as pre-de-epidermalized dermis or collagen/fibroblast mixed lattices. In the collagen/fibroblast mixed lattices, the combination of native collagen and isolated human fibroblasts leads to a dermis equivalent being obtained which mimics a dermis which has not been subjected to the action of time.

Reconstructed skin models generally exhibit a deficient barrier function (M. Ponec, P. J. J. Wauben-Penris, A. Burger, J. Kempenarr, H. E. Bodde, *Skin Pharmacol.*, 1990; 3: pp. 126–135). This deficiency is largely due to important modifications in the ceramide profile of this model which have been observed compared to a normal human epidermis.

In addition, it is known from the prior art that atopic, xerotic and aged skin may be associated with a decrease in synthesis of ceramides 1 and/or 3. Mention may, for example, be made of the following documents:

Imokawa et al., in *J. Invest. Dermatol.*, 96 (4): 523–6, 1991, disclose that ceramides are involved in the barrier function and that their synthesis, in particular that of ceramide 1, is decreased in the case of atopic and xerotic skin.

Di Nardo et al., in *Acta Derm. Venereol.*, 78(1): 27–30, 1998), describe atopic dermatitis as readily irritable and dry skin in which the barrier function is impaired. The authors showed that a decrease in the synthesis of ceramides 1 and 3 may be the cause of the dry skin and of the barrier function impairment in atopic dermatitis.

Rogers et al., in *Arch. Dermatol. Res.*, 288:765–770, 1996, describe a decrease in the synthesis of ceramides, in particular ceramide 1, which contributes, in aged skin, to a disturbance of the barrier function and to xerosis, particularly during the winter months.

Rogers et al., in *J. Invest. Dermatol.*, 100:510, 1993 disclose that the lipid multilayer structure of dry skin is disturbed, and that this disturbance is accompanied by an increase in free fatty acids and by a decrease in ceramides.

In order to improve aged skin, dry skin and skin sensitivity, compositions are already known which contain a precursor for ceramide synthesis selected from: the sphinganine and sphingosine bases, fatty acid amides, and vitamin $B_3$ as a ceramide synthesis stimulator (WO 99/47114), as are compositions which contain an intermediate of the synthetic pathways, or precursor, for ceramides chosen from fatty acids, the sphinganine and sphingosine bases, and vitamin A as a ceramide synthesis stimulator (WO 94/23694).

M. Ponec et al., in *Skin Pharmacol.*, 1990; 3: pp. 126–135, disclose, moreover, that reconstructed skin models generally exhibit a deficient barrier function. This deficiency is largely due to important modifications of the ceramide profile of this model which have been observed compared to a normal human epidermis.

It is also known practice, from FR-2,811,556, to use 6-hydroxy-4-sphingenine to enhance the barrier function of reconstructed skin and to reinforce the lipid barrier of the epidermis, in particular of dry and/or rough and/or damaged skin, and/or to re-establish or maintain the integrity of the stratum corneum, and/or to improve the surface appearance and/or moisturization of the skin, and/or to protect the skin, in particular dry and rough skin, and/or as a nutritive agent essential for keratin substances (skin, hair, eyelashes, nails), and/or to reinforce the lipid barrier of reconstructed skin or skin equivalent, and/or to enhance and/or maintain the lipid content of human epidermis, in vivo and in vitro, and/or to improve the quality and the properties, such as the lipid content and/or barrier property content of reconstructed epidermis and/or epidermal cell cultures.

However, in using 6-hydroxy-4-sphingenine, it is not possible to control the nature of the ceramide which will be obtained in situ subsequent to its combination with a fatty acid in the epidermis. 6-Hydroxy-4-sphingenine is in fact the constitutive sphingoid base of several ceramides: ceramides STAR, 4, 5.5 and 7 ("The Normal Human stratum corneum: a new ceramide profile" M. Chopart et al., Prospectives in Percutaneous Penetration, 8th International Conference Antibes Juan-Les Pins, France, 2–6 Apr. 2002 and document JP2000/143,598 by Kanebo). In addition, reconstructed skin is a fragile structure whose survival can only be maintained for a limited period of time (approximately 1 month). Any gain in time which allows reconstructed skin to acquire a barrier function is therefore an important parameter in relation to its lifespan.

In order to improve the lipid profile of reconstructed epidermis, it is also known practice to add ascorbic acid or vitamin C (*J. Invest. Dermatol.*, 109:348–355, 1997) or ascorbic acid derivatives (FR-2,807,320) to the culture medium.

However, because of its chemical structure (alpha-keto-lactone), ascorbic acid is very sensitive to certain environmental parameters such as light, heat and aqueous media, in particular alkaline and/or aerobic media. Because of these problems of stability, it is necessary to use high concentrations of ascorbic acid in order to observe the effect on the skin of a composition containing it. In addition, in introducing ascorbic acid or one of its derivatives into the culture medium, it is not possible to control the exact nature of the ceramide which will be synthesized in situ.

There remains therefore a need for other methods for obtaining more rapidly reconstructed skin models for which the ceramide profile is improved, with a barrier function which comes close to normal human epidermis.

SUMMARY OF THE INVENTION

A novel method for preparing a reconstructed epidermis or a skin equivalent supplemented with at least one derivative of ceramide 7 and/or 5.5 has now been discovered, comprising introducing into the culture medium at least one derivative of ceramide 7 and/or 5.5 and/or in topically applying to said reconstructed epidermis or said skin equivalent a composition based on lipid lamellar vesicles incorporating at least one derivative of the ceramide 7 and/or 5.5 family.

By virtue of the novel method of preparation, it is now possible to obtain a skin equivalent, or a reconstructed skin, supplemented with at least one derivative of ceramide 5.5 and/or 7 of formula (I), preferably a derivative of ceramide 7 of formula (I), by exactly controlling the nature of the ceramide whose proportion increases in said skin equivalent or said reconstructed skin.

It has also now been determined that a composition based on lipid lamellar vesicles incorporating at least one derivative of the ceramide 7 and/or ceramide 5.5 family makes it possible to improve the barrier function of an epidermis exhibiting a deficiency in 6-hydroxy-4-sphingenine-base ceramides. This is particularly advantageous since it has been shown, in the context of the invention, that dry skin and reconstructed skin (study carried out on the EPISKIN™ model) exhibit a deficiency in the most polar ceramides, which results in a deficiency in 6-hydroxy-4-sphingenine (also called 6-hydroxy-4-sphingosine) sphingoid bases.

DETAILED DESCRIPTION OF BEST MODE AND SPECIFIC/PREFERRED EMBODIMENTS OF THE INVENTION

Thus, the present invention features a method for preparing a reconstructed epidermis or a skin equivalent supplemented with at least one derivative of ceramide 7 and/or 5.5 of formula (I), comprising introducing at least one derivative of ceramide 7 and/or 5.5 into the culture medium of said reconstructed epidermis or said skin equivalent and/or in topically applying to the surface of said reconstructed epidermis or of said skin equivalent a composition based on lipid lamellar vesicles incorporating at least one derivative of the ceramide 7 and/or 5.5 family of formula (I) below:

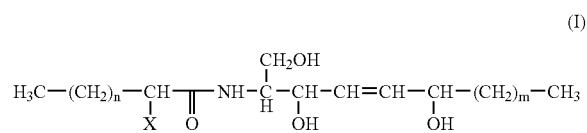

(I)

in which X is a hydrogen atom or a hydroxyl (OH) group; advantageously a hydroxyl group; n is an integer ranging from 19 to 29, preferably from 21 to 27, advantageously equal to 21, 22 or 23; and m is an integer ranging from 9 to 19, preferably from 9 to 15, advantageously equal to 11, 12 or 13.

The derivatives of ceramide 5.5 of formula (I) are those for which X represents an hydrogen atom. The derivatives of ceramide 7 of formula (I) are those for which X represents a hydroxyl group.

According to a preferred embodiment, the compounds of formula (I) are those for which n ranges from 21 to 27 and m ranges from 9 to 15.

According to another preferred embodiment, the compounds of formula (I) are those for which n is equal to 21, 22 or 23 and m is equal to 11, 12 or 13. Ceramide 7, as described by Robson et al., in *J. Lipid Res.*, 1994 35:2060–2068, corresponding to the compound of formula (I) for which n is equal to 21 and m is equal to 11, is particularly preferred according to the invention.

According to the methods of the invention, the concentration of at least one derivative of formula (I) introduced into the culture medium is from 10 g/l to $10^{-6}$ g/l, preferably from 1 g/l to $10^{-5}$ g/l, advantageously from $10^{-1}$ g/l to $10^{-5}$ g/l of culture medium.

The introduction into the culture medium of at least one derivative of ceramide 5.5 and/or 7 of formula (I) may be carried out by various methods, which will be chosen in such a way that the derivative of ceramide 5.5 and/or 7 of formula (I) is, in the end, solubilized in the culture medium. In fact, due to the lipophilic structure of the derivatives of ceramide 5.5 and/or 7 of formula (I), it is understood that this dissolution in the culture medium is not, a priori, evident. According to a first variant, said derivative is dissolved beforehand in a solvent. In another variant, said derivative is combined beforehand with another molecule capable of transporting it. Another variant entails preparing beforehand a composition based on lipid lamellar vesicles incorporating at least said derivative of the ceramide 7 and/or 5.5 family. These compositions, combinations and/or solvations thus obtained beforehand are then introduced into the culture medium.

The solvent chosen should be capable of solubilizing the ceramide 7 and/or 5.5 of formula (I). The solution obtained is then introduced into the culture medium. The amount of solvent introduced into the culture medium is such that it does not hinder the normal development of the epidermis and its homeostasis. Advantageously, the ceramide 7 and/or 5.5 of formula (I) may be dissolved in ethanol or DMSO at the desired concentration; the final ratio of solvent introduced into the culture medium must not exceed 1/1000.

The method according to the invention may also entail introducing into the culture medium a combination prepared beforehand, containing at least one said derivative and at least one molecule capable of transporting said derivative and making it bioavailable within the reconstructed epidermis or said skin equivalent from the culture medium.

The molecules capable of transporting said derivative and making it bioavailable are advantageously chosen from BSA (Bovine Serum Albumin) and/or a compound of the cyclodextrin family or a derivative of the cyclodextrin family allowing transport and solubilization in the culture medium in a similar manner.

When the ceramide 7 and/or 5.5 of formula (I) is combined with BSA, the molar ratio with respect to BSA is, for example, from 1/1000 to 1/3, preferably 1/100 to 1/5. The concentration of BSA which may be introduced into the culture medium should be less than or equal to 100 µmol/l, preferably from 0.5/µmol/l to 100 µmol/l, preferentially from 10 µmol/l to 50 µmol/l.

When the ceramide 7 and/or 5.5 of formula (I) is combined with at least one compound of the cyclodextrin family, advantageously HPBCD or 12-hydroxypropyl-β-cyclodextrin, or a derivative of the cyclodextrin family, allowing transport and solubilization in the culture medium in a similar manner, the approximate concentration of ceramide 7 and/or 5.5 of formula (I) may, for example, be from 0.01 nmol/µl to 100 nmol/µl, preferably from 0.1 nmol/µl to 10 nmol/µl, and more particularly from 1 nmol/µl to 5 nmol/µl of a 50% solution of cyclodextrins (diluted in water). This concentration will of course be adjusted as a function of the chosen derivative and of the secondary composition of the culture medium itself. This preparation is then introduced into the culture medium, the volume thus introduced being adjusted to the desired final concentration of ceramide 7 and/or 5.5 of formula (I).

The combinations described above, made up of the ceramide 7 and/or 5.5 of formula (I) and a vehicle, may also comprise:

an antioxidant, advantageously DL-α-tocopherol acetate at a concentration of less than or equal to 50 µmol/l, preferably from 0.5 µmol/l to 50 µmol/l of culture medium, advantageously 21 µmol/l of culture medium, and/or a cellular transporting agent, advantageously L-carnitine at a concentration of less than or equal to 100 µmol/l, preferably from 0.5 to 100 µmol/l, advantageously 10 µmol/l of culture medium.

When the method according to the invention entails introducing into the culture medium a composition based on lipid lamellar vesicles incorporating at least one derivative of the ceramide 7 and/or 5.5 family, said composition preferably comprises a dispersion, in an external aqueous phase, of vesicles formed by lipid lamellar phases separated from one another by hydrophilic layers, said lamellar phases comprising at least one amphiphilic lipid, and at least said derivative of formula (I) included in said lipid lamellar phases.

The abovementioned concentrations may be adjusted (increased or decreased) so as to remain within a concentration range such that they do not hinder the normal development of the epidermis and its homeostasis.

The culture medium according to the invention is a medium well known to those skilled in the art. It is in particular a medium as described in one of the following documents: EP-A-285471, EP-A-285474, EP-A-789074, EP-A-502172, EP-A-418035, WO-A-9116010, EP-A-197090, EP-A-20753, FR-A-2665175, FR-A-2689904 FR-A-2792650 and FR-2,811,556. See also U.S. Pat. Nos. 5,861,153, 6,605,466 and 6,660,522

According to another embodiment of the method according to the invention, the reconstructed skin supplemented with at least one ceramide 7 and/or 5.5 of formula (I) is obtained by topical application to the surface of the epidermis in culture of a composition based on lipid lamellar vesicles incorporating at least one derivative of the ceramide 7 and/or 5.5 family. Advantageously, said composition comprises a dispersion, in an external aqueous phase, of vesicles formed by lipid lamellar phases separated from one another by hydrophilic layers, said lamellar phases comprising at least one amphiphilic lipid, and at least said derivative of formula (I) included in said lipid lamellar phases.

The present invention also features compositions comprising a dispersion, in an external aqueous phase, of vesicles formed by lipid lamellar phases separated from one another by hydrophilic layers, said lamellar phases comprising at least one amphiphilic lipid, and at least one derivative of formula (I) as defined above, included in said lipid lamellar phases.

The compositions according to the invention may be used most particularly for skincare. In particular, the compositions according to the invention may make it possible to improve the barrier function of dry skin, of rough and/or damaged and/or aged and/or sensitive and/or atopic skin, of reconstructed skin or skin equivalents, and also any epidermis exhibiting even a slight deficiency in 6-hydroxy-4-sphingenine-base ceramides, or to further reinforce the barrier function of normal human skin.

This invention therefore also features the use (regime or regimen) of said composition for:

reinforcing the barrier function of normal human epidermis, and/or reinforcing the barrier function of reconstructed skin or skin equivalents, advantageously the reconstructed skin is the EPISKIN™ model, and/or improving the barrier function of an epidermis exhibiting even a slight deficiency in 6-hydroxy-4-sphingenine-base ceramides, preferably of dry skin, or of rough and/or damaged and/or aged and/or sensitive skin, and/or re-establishing or maintaining the integrity of the stratum corneum, and/or improving the surface appearance and/or the moisturization of the skin, and/or improving or maintaining the lipid content of human epidermis, in vivo and in vitro, and/or improving the quality and the properties, such as the lipid content and/or barrier property, of reconstructed epidermis and/or of epidermal cell cultures.

This invention also features the use of the compositions according to the invention for producing a formulation intended for the treatment of atopic skin.

It is well established that reconstructed skin represents a model which is close to human skin. As a result, a composition according to the invention, capable of increasing the barrier function of reconstructed skin, is also of value for normal human epidermis, and also for any epidermis exhibiting even a slight deficiency in 6-hydroxy-4-sphingenine-base ceramides, in particular epidermis of dry and/or rough and/or damaged and/or aged and/or sensitive skin, and/or of atopic skin, by maintaining or re-establishing a ceramide profile such that it makes it possible to increase or maintain their barrier function.

The present invention also features a cosmetic treatment for making human skin more attractive or moisturizing it, characterized in that it entails applying topically to the skin a composition as defined above.

The term "vesicle" or "vesicular dispersion" is intended to mean a dispersion of amphiphilic lipids forming, on contact with water or with a hydrophilic medium, particles the core of which is hydrophilic (water or hydrophilic mixture) and the wall of which consists of bilayers of lamellar liquid crystal type. These vesicles are commonly called liposomes. They consist mainly of natural or synthetic phospholipids, which may or may not be hydrogenated. As regards niosomes, they consist of nonionic surfactants optionally combined with cholesterol and/or an ionic surfactant.

The vesicles according to the invention are formed by, or comprise, from one to twenty five leaflets of lamellar phases which are substantially concentric, of bimolecular type.

The vesicles according to the invention may be either niosomes of the type such as those described in EP-O-958,856, EP-O-582,503, EP-O-455,528 and EP-O-043,327, or liposomes of the conventional type. The derivatives of formula (I) according to the invention become, in this type of structure, one of the constituents of the lamellar phases.

The amount of derivative of formula (I) ranges from 0.001% to 30%, preferably 0.001% to 10%, advantageously from 0.001% to 5%, relative to the total weight of the lipid composition constituting the vesicles.

The weight ratio of the amount of lipid phase to the amount of aqueous phase of the dispersion is from 1/1000 to 300/1000.

The vesicular dispersions according to the invention may be prepared according to many methods well known to those skilled in the art. For example, according to a first method, all the amphiphilic lipids, including the derivatives of formula (I) according to the invention, are dissolved in a volatile solvent, a thin lipid film is formed on the walls of a flask by evaporation of the solvent, and then the lipid film is taken up in an aqueous solution of octylglucoside so as to form octylglucoside/vesicular lipid mixed micelles. This solution is then dialyzed against distilled water. The liposomes form as the octylglucoside is dialyzed. This method is particularly suitable when only a very small amount of derivatives of formula (I) is available.

This method is not, however, limiting, and the other methods used to form vesicular dispersions (liposomes) can be envisaged (Bangham, by injection of ethanol, by fusion, by "reverse phase" etc.). Mention may also be made of the method described in EP-O-582,503 B1.

As demonstrated on reconstructed skin, the compositions according to the invention based on lipid lamellar vesicles incorporating at least one derivative of formula (I) make it possible to improve the quality of the epidermis where simple topical application of said derivative of formula (I) provides no improvement of said epidermis.

The incorporation of at least one said derivative of formula (I) into lipid lamellar phases makes it possible to obtain the desired effect on improvement of the barrier function of the reconstructed epidermis while at the same time taking into account the intrinsic characteristics of the derivatives of formula (I): large molecules, difficult to formulate and to stabilize.

A vesicular dispersion according to the invention also makes it possible to improve the bioavailability of the derivatives of formula (I) within the layers of the epidermis. Said bioavailability is improved since the formula of the vesicular dispersion according to the invention represents a formula similar to the multilayer lipid structures of the epidermis which represent the target of said derivatives of formula (I).

In addition, the derivatives of formula (I) are markedly amphiphilic in nature, which has the advantage of facilitating their incorporation into the epidermis.

Thus, the vesicular dispersion according to the invention containing at least one derivative of formula (I) makes it possible to control the nature of the ceramide which is specifically provided within the multilayer lipid structures of the epidermis.

For the purpose of the invention, the term "bioavailability" is intended to mean the penetration of an active agent into the skin so that said active agent is biologically available for the living elements of the skin, and in particular the epidermis. Thus, increasing the bioavailability of an active agent has the effect of increasing the amount of active agent which will reach the living epidermis.

In addition, the compositions according to the invention make it possible to make the ceramide 5.5 and/or 7 available directly within the cornified layer in a situation where, without suitable formulation, said ceramide does not penetrate into the cornified layer. Thus, the compositions according to the invention make it possible to make good, directly in the cornified layer, a deficiency in ceramide 5.5 and/or 7.

The composition may be applied topically to the surface of the epidermis in culture in an amount from 0.5 µl to 10 µl, preferably 1 µl to 5 µl, and more particularly of 2 µl per cm² of reconstructed epidermal surface. The composition is then generally made homogeneous at the epidermal surface by spreading using a spatula.

The derivatives of formula (I) according to the invention can be isolated by TLC from lipid samples taken by noninvasive methods from normal volunteers, according to a method well known to those skilled in the art. These lipid samples are then subjected to a preparative and analytical treatment for isolating the derivatives of formula (I) from the other lipids and purifying them. These methods are, for example, described in JP-2000/143,598 or M. Chopart et al., "Prospectives in Percutaneous Penetration," 8th International Conference Antibes Juan-Les Pins, France, 2–6 Apr. 2002, and JP-2000/143,598 by Kanebo).

The derivatives of formula (I) can also be prepared according to methods of conventional organic synthesis, for example by a condensation reaction between a fatty acid of formula (II) and a base of formula (III), preferably the base 6-hydroxy-4-sphingenine.

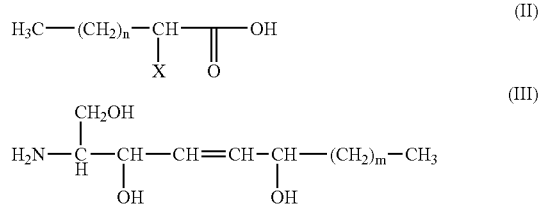

X, n and m are as defined above.

The 6-hydroxy-4-sphingenine base can be prepared according to methods of synthesis described and well known to those skilled in the art, for example as described or inspired by "Mendeleev, *Commun.*, 108–110, 1992" or "*Tetrahedron Letters,* 34, No. 7, 1191–1194, 1993".

The fatty acids are widely commercially available.

Another method of conventional organic synthesis, described in JP-2000/143,598, consists of a reaction comprising oxidation in the 6-position of the base using a nonoxidized precursor.

The derivative of formula (I) may be introduced at any moment during the lifetime of the skin equivalent (a maximum of 2 months), whether it is in the immersion or emersion state, according to at least one of the methods according to the invention by topical application and/or introduction into the culture medium. Preferably, the ceramide 7 and/or 5.5 of formula (I) may be introduced into the skin equivalent between the 1st day of culturing and the thirtieth day of culturing, and more particularly between the fourth day and the twenty-first day.

The direct supplementation in the culture medium may take place each time the culture medium is changed, which generally occurs every two days. This supplementation may be increased or decreased as a result of the changes of culture medium occurring as a function of the desired effect and of the requirements of studies or of certain methods of production.

The supplementation by topical administration may preferably take place every two days. Here again, this frequency will be adjusted, ranging from one supplementation every hour to every week, as a function of the desired effects and of the requirements of studies or of certain methods of production.

According to a preferred embodiment of the invention, the method is carried out on the EPISKIN™ reconstructed epidermis model.

The compounds of formula (I) as defined above therefore have the great advantage of providing investigators with a new skin equivalent, supplemented with at least one derivative of formula (I). According to the method of the invention, the amount of ceramide 7 and/or 5.5 which may be introduced into the stratum corneum of the reconstructed skin represents from 0.1 µg to 50 µg per mg of stratum corneum, advantageously from 0.5 µg to 15 µg per mg of stratum corneum.

Preferably, the skin equivalent or reconstructed skin supplemented with at least one derivative of the ceramide 5.5 or 7 family of formula (I) obtained according to one of the methods of the invention contains an amount of ceramide 5.5 or 7 of formula (I) greater than 1% of the total ceramides.

The present invention is also based on the observation that reconstructed skin exhibits a clear deficiency in the most polar ceramides, which results in a deficiency in 6-hydroxy-4-sphingenine sphingoid bases making up these ceramides, essentially to the benefit of the 4-sphingenine base (also called sphingosine). The results obtained are given in FIG. 1. FIG. 1 shows a comparison of the relative profiles of the ceramide-derived sphingoid bases derived from normal human stratum and EPISKIN™.

The applicant has discovered that the derivatives of the ceramide 5.5 family of formula (I) with X=H as defined above make it possible to reinforce the barrier function of reconstructed skin, also called skin equivalent.

In fact, it has been noted that supplementing said reconstructed skin with at least one derivative of formula (I) with X=H as defined above makes it possible to improve the appearance and the barrier properties of this said skin, and to make it more structurally similar to normal skin.

It is thus possible to obtain a new skin equivalent, or new reconstructed skin, containing at least one derivative of ceramide 5.5 of formula (I) with X=H as defined above.

The present invention therefore features a skin equivalent or reconstructed skin containing at least one derivative of formula (I) with X=H as defined above, n and m, moreover, being as defined above. Preferably, the skin equivalent or reconstructed skin contains an amount of ceramide 5.5 of formula (I) greater than 1% of the total ceramides.

Said skin equivalent or said reconstructed skin containing at least one derivative of formula (I) with X=H may be obtained using one of the methods as described above.

The amphiphilic lipids constituting the vesicular dispersions according to the invention are well known to those skilled in the art. For example, these amphiphilic lipids may be based on natural or synthetic phospholipids, which may or may not be hydrogenated, and/or on nonionic surfactants which may or may not be combined with cholesterol.

The ionic, cationic, anionic or nonionic amphiphilic lipids which are preferred according to the invention are chosen from those described in EP-0-582,503 µl, FR-2-485,921 and FR-2-315,991.

The preferred anionic amphiphilic lipids (B) are selected from the group consisting of:
alkali salts of dicetyl and dimyristyl phosphate;
alkali salts of cholesterol sulphate;
alkali salts of cholesterol phosphate;

lipoamino acids and their salts, such as monosodium and disodium acylglutamates, for instance the disodium salt of N-stearoyl-L-glutamic acid sold under the name Acylglutamate HS21 by AJINOMOTO;

sodium salts of phosphatidic acid;

phospholipids;

alkylsulphonic derivatives in particular of formula (X):

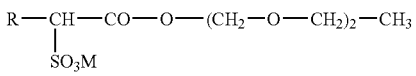

in which R represents $C_{16}$–$C_{22}$ alkyl radicals, in particular the radicals $C_{16}H_{33}$ and $C_{18}H_{37}$, taken as a mixture or separately, and M is an alkali or alkaline-earth metal such as sodium; and mixtures thereof.

The cationic amphiphilic lipids according to the invention are preferably selected from the group consisting of quaternary ammonium salts, and fatty amines and their salts.

The quaternary ammonium salts are, for example:

those which have the general formula (XI) below:

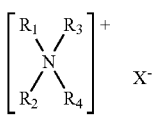

in which the radicals $R_1$ to $R_4$, which may be identical or different, are each a linear or branched aliphatic radical having from 1 to 30 carbon atoms, or an aromatic radical such as aryl or alkylaryl. The aliphatic radicals may comprise hetero atoms such as, in particular, oxygen, nitrogen, sulphur or halogens. The aliphatic radicals are, for example, chosen from alkyl, alkoxy, polyoxy($C_2$–$C_6$)alkylene, alkylamide, ($C_{12}$–$C_{22}$)alkylamido($C_2$–$C_6$)alkyl, ($C_{12}$–$C_{22}$)alkyl acetate and hydroxyalkyl radicals having approximately from 1 to 30 carbon atoms; X is an anion selected from the group consisting of halides, phosphates, acetates, lactates, ($C_2$–$C_6$)alkyl sulphates, alkyl sulphonates and alkylaryl sulphonates;

the quaternary ammonium salts of imidazolinium, such as, for example, that of formula (XII) below:

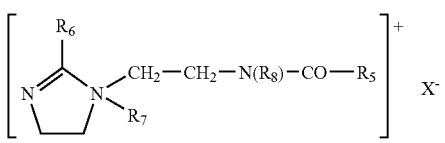

in which $R_5$ is an alkenyl or alkyl radical having from 8 to 30 carbon atoms, for example fatty acid derivatives of tallow, $R_6$ is a hydrogen atom, a $C_1$–$C_4$ alkyl radical or an alkenyl or alkyl radical having from 8 to 30 carbon atoms, $R_7$ is a $C_1$–$C_4$ alkyl radical, $R_8$ is a hydrogen atom or a $C_1$–$C_4$ alkyl radical, X is an anion selected from the group consisting of halides, phosphates, acetates, lactates, alkyl sulphates, alkyl sulphonates or alkylaryl sulphonates. $R_5$ and $R_6$ preferably denote a mixture of alkenyl or alkyl radicals having from 12 to 21 carbon atoms, for example fatty acid derivatives of tallow, $R_7$ is methyl, and $R_8$ is hydrogen. Such a product is sold, for example, under the name "REWOQUAT W75" by REWO;

the diquaternary ammonium salts of formula (XIII) below:

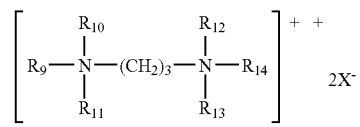

in which $R_9$ is an aliphatic radical having approximately from 16 to 30 carbon atoms, $R_{10}$, $R_{11}$, $R_{12}$, $R_{13}$ and $R_{14}$, which may be identical or different, are each hydrogen or an alkyl radical having from 1 to 4 carbon atoms, and X is an anion selected from the group consisting of halides, acetates, phosphates, nitrates and methyl sulphates. Such diquaternary ammonium salts comprise in particular propanetallowdiammonium dichloride;

the quaternary ammonium salts containing at least one ester function.

The quaternary ammonium salts containing at least one ester function which can be used according to the invention are, for example, those which correspond to the formula (XIV) below:

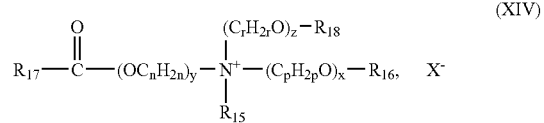

in which $R_{15}$ is a $C_1$–$C_6$ alkyl radical or a $C_1$–$C_6$ hydroxyalkyl or dihydroxyalkyl radical; $R_{16}$ is the radical $R_{19}$—CO—; a linear or branched, saturated or unsaturated $C_1$–$C_{22}$ hydrocarbon-based radical $R_{20}$; a hydrogen atom; $R_{18}$ is the radical $R_{21}$, —CO—; a linear or branched, saturated or unsaturated $C_1$–$C_6$ hydrocarbon-based radical $R_{22}$; a hydrogen atom; $R_{17}$, $R_{19}$ $_{and}$ $_{R20}$, which may be identical or different, are each a linear or branched, saturated or unsaturated $C_7$–$C_{21}$ hydrocarbon-based radical; n, p and r, which may be identical or different, are integers ranging from 2 to 6; y is an integer ranging from 1 to 10; x and z, which may be identical or different, are integers ranging from 0 to 10; and $X^-$ is a simple or complex, organic or mineral anion; with the proviso that the sum x+y+z ranges from 1 to 15, and that, when x is 0, then $R_{16}$ denotes $R_{20}$, and that, when z is 0, then $R_{18}$ denotes $R_{22}$.

The alkyl radicals $R_{15}$ may be linear or branched, and more particularly linear.

$R_{15}$ preferably denotes a methyl, ethyl, hydroxyethyl or dihydroxypropyl radical, and more particularly a methyl or ethyl radical.

Advantageously, the sum x+y+z ranges from 1 to 10.

When $R_{16}$ is a hydrocarbon-based radical $R_{20}$, it may be long and may contain from 12 to 22 carbon atoms, or may be short and may contain from 1 to 3 carbon atoms.

When $R_{18}$ is a hydrocarbon-based radical $R_{22}$, it preferably contains 1 to 3 carbon atoms.

Advantageously, $R_{17}$, $R_{19\ 9}$ and $R_{21}$, which may be identical or different, are each a linear or branched, saturated or unsaturated $C_{11}$–$C_{21}$ hydrocarbon-based radical, and more particularly a linear or branched, saturated or unsaturated $C_{11}$–$C_{21}$ alkyl or alkenyl radical.

Preferably, x and z, which may be identical or different, are equal to 0 or 1. Advantageously, y is equal to 1.

Preferably, n, p and r, which may be identical or different, are equal to 2 or 3, and even more particularly are equal to 2.

The anion is preferably a halide (chloride, bromide or iodide) or an alkyl sulphate, more particularly methyl sulphate. However, methanesulphonate, phosphate, nitrate, tosylate, an anion derived from an organic acid, such as acetate or lactate, or any other anion compatible with the ammonium containing an ester function, may be used.

The anion $X^-$ is even more particularly chloride or methyl sulphate.

Particularly preferred ammonium salts of formula (XIV) are those in which:

$R_{15}$ denotes a methyl or ethyl radical, x and y are equal to 1;

z is equal to 0 or 1;

n, p and r are equal to 2;

$R_{16}$ is the radical $R_{19}$—CO—; a methyl, ethyl or $C_{14}$–$C_{22}$ hydrocarbon-based radical; or a hydrogen atom;

$R_{18}$ is the radical $R_{21}$—CO—; or a hydrogen atom; and $R_{17}$, $R_{19}$ and $R_{21}$, which may be identical or different, are each a linear or branched, saturated or unsaturated $C_{13}$–$C_{17}$ hydrocarbon-based radical, and preferably a linear or branched, saturated or unsaturated $C_{13}$–$C_{17}$ alkyl or alkenyl radical.

Advantageously, the hydrocarbon-based radicals are linear.

Mention may, for example, be made of the compounds of formula (XIV) such as the diacyloxyethyl-dimethylammonium, diacyloxyethylhydroxyethylmethyl-ammonium, monoacyloxyethyldihydroxyethylmethylammonium, triacyloxyethylmethylammonium and monoacyloxyethyl-hydroxyethyldimethylammonium salts (chloride or methyl sulphate in particular), and mixtures thereof. The acyl radicals preferably contain 14 to 18 carbon atoms and originate more particularly from a plant oil such as palm oil or sunflower oil. When the compound contains several acyl radicals, these radicals may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization using an alkylating agent such as an alkyl halide (preferably a methyl or ethyl halide), a dialkyl sulphate (preferably dimethyl or diethyl sulphate), methyl methane-sulphonate, methyl para-toluenesulphonate, glycol chlorohydrin or glycerol chlorohydrin.

Such compounds are, for example, sold under the names DEHYQUART by HENKEL, SEPANQUAT by STEPAN, NOXAMIUM by CECA or REWOQUAT WE 18 by REWO-WITCO.

The nonionic amphiphilic lipids (A) making up the membrane of the vesicles according to the invention are preferably selected from the group consisting of:

the esters and/or the ethers of a polyol and of a fatty acid, which may or may not be polyoxyethylenated;

the esters and/or the ethers of a fatty acid of an α-butylglycoside;

synthetic or natural phospholipids, which may or may not be hydrogenated.

The esters or the ethers of a polyol and of a fatty acid are preferably selected from mixtures of esters or mixtures of ethers of at least one polyol selected from the group consisting of polyethylene glycol comprising from 1 to 60 ethylene oxide units, sorbitan, sorbitan bearing 2 to 60 ethylene oxide units, glycerol bearing 2 to 30 ethylene oxide units, polyglycerols comprising 2 to 15 glycerol units, sucroses, and glucoses bearing 2 to 30 ethylene oxide units, and at least one fatty acid comprising a linear or branched, saturated or unsaturated $C_5$–$C_{22}$ alkyl chain, the number of alkyl chains per polyol group being between 1 and 10.

The esters of a polyol and of a $C_5$–$C_{22}$ fatty acids which are particularly preferred are those corresponding to formula (XV) below:

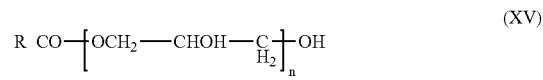

(XV)

where n is a statistical value which may contain various proportions of esters for which n=1, n=2, n=3, n=4, etc.; this is also the case of esters comprising several alkyl chains in their lipophilic component, such as cocoates, which contain $C_5$–$C_{22}$ alkyl chains, or isostearates where the alkyl chains are $C_{17}$ chains are a complex mixture of isomeric forms; this is also the case of products consisting of mixtures of mono-, di-, tri- or polyesters of the same polyol.

Among the commercial products which can be used according to the invention and which have the structure of a mixture of esters of a polyol and of a $C_5$–$C_{22}$ fatty acid as defined above, mention may be made of:

partial esters of sorbitan (or sorbitol anhydride) and of a fatty acid, sold under the commercial names "SPAN 20, 40, 60 and 80" by "ICI";

sorbitan isostearate, sold under the trademark "SI 10 R NIKKOL" by "NIKKO";

sorbitan stearate bearing 4 units of ethylene oxide, sold under the name "TWEEN 61" by "ICI1";

polyethylene glycol stearate containing 8 ethylene oxide units, sold under the name "MYR J 45" by "ICI";

the polyethylene glycol monostearate of formula (XVI) below:

$$HOCH_2\text{—}(CH_2OCH_2)_n CH_2OH \qquad (XVI)$$

in which n is equal to 4, sold under the name "MYS 4" by "NIKKO";

polyethylene glycol (molecular weight 400) stearate, chemical quality or quality produced by biotechnology, sold by "UNICHEMA";

diglyceryl stearate bearing 4 ethylene oxide units, sold under the name "HOSTACERINE DGS" by "HOECHST";

tetraglyceryl stearate, sold under the name "TETRAGLYN IS" by "NIKKO";

diglyceryl isostearate, sold by "SOLVAY";

diglyceryl distearate, sold under the name "EMALEX DSG 2" by "NIHON";

sucrose mono-, di- and tripalmitostearate, sold under the names "F50, F70, F110 and F160 CRODESTA" by "CRODA";

the mixture of sucrose mono- and dipalmito-stearate sold under the name "GRILLOTEN PSE 141 G" by "GRILLO";

the mixture of sucrose stearate and sucrose cocoate, sold under the name "ARLATONE 2121" by "ICI";

methylglucose distearate bearing 20 ethylene oxide units, sold under the name "GLUCAM E20 DISTEARATE" by "AMERCHOL".

The esters and the ethers of a fatty acid of an α-butylglucoside used according to the invention are preferably either mixtures of esters and/or mixtures of ethers of various fatty acids of an α-butylglucoside, the various fatty chains of which comprise, with respect to one another, a similar number of carbon atoms (for example different by 1 or 2), or mixtures of mono-, di-, tri- or polyesters and/or mixtures of mono-, di-, tri- or polyethers of the same fatty acid of an α-butylglucoside.

The esters and the ethers of a fatty acid of an α-butylglucoside according to the invention preferably comprise a fatty chain containing from 8 to 24 carbon atoms, more preferably from 12 to 22 carbon atoms, and more particularly from 14 to 18 carbon atoms.

Mention may be made, for example, of the esters and the ethers of the lauric ($C_{12}$), myristic ($C_{14}$), palmitic ($C_{16}$), stearic ($C_{18}$) or behenic ($C_{22}$) acid of an α-butylglucoside.

Use is more particularly made of a mixture of a mono- and diester of the palmitic acid of an α-butyl-glucoside obtained according to the enzymatic method of production described, in the lipid vesicles in accordance with the invention.

The esters and the ethers of a fatty acid of an α-butylglucoside in accordance with the invention may be prepared from an α-butylglucoside obtained according to the enzymatic method of production described in FR-A-2680373, which entails bringing butanol into contact with starch, malto-dextrins or maltose in the presence of a purified enzyme preparation having α-transglucosylation activity. The esters and the ethers of a fatty acid of an α-butylglucoside can be synthesized by reacting the fatty acid or the corresponding fatty acid mixture with the a-butylglucoside according to conventional methods.

The synthetic or natural phospholipids, which may or may not be hydrogenated, which are preferred according to the invention are chosen from lecithin, preferably hydrogenated lecithin, combined either with cholesterol and, optionally, with an ionic surfactant, and an oxyethylenated phytosterol comprising from 2 to 50 ethylene oxide units.

The amphiphilic lipids described in FR-2-315,991 and FR-2-485,921 should also be added to this list.

In a known manner, for producing the vesicular dispersions according to the invention, use may be made of mixtures of ionic amphiphilic lipids, mixtures of nonionic amphiphilic lipids and mixtures of these two types of lipids.

According to a preferred embodiment of the invention, the weight ratio of the amount of nonionic amphiphilic lipid (A) to the amount of ionic amphiphilic lipid (B) is from 50/1 to 50/25.

It is possible, in a known manner, to incorporate into the lipid phase constituting the lipid membrane of the aqueous-core vesicles of the invention, at least one additive, the main function of which is to decrease the permeability of the vesicles, to prevent flocculation and fusion thereof, and to increase the degree of encapsulation.

According to a preferred embodiment of the invention, it is possible to add to the lipid phase at least one additive preferably selected from the group consisting of:
 sterols, and in particular phytosterols and cholesterol,
 long-chain alcohols and diols,
 long-chain amines and quaternary ammonium derivatives thereof.

These additives may optionally have a cosmetic and/or dermopharmaceutical activity. This is, for example, the case of cholesterol.

The amount of these additives ranges from 0% to 50% relative to the total weight of the lipid composition constituting the aqueous-core vesicles.

In the compositions according to the invention, the aqueous-core vesicles preferably have a mean diameter ranging from 10 to 5,000 nm.

Advantageously, the vesicular dispersion according to the invention may also contain at least one other ceramide chosen from the ceramides STAR, 1, 2, 2.5, 3, 4, 5 and/or 6 (as described in the document "The Normal Human stratum corneum: a new ceramide profile", M. Chopart et al., Prospectives in Percutaneous Penetration, 8th International Conference, Antibes, Juan-Les Pins, France, 2–6 Apr. 2002), advantageously the ceramides STAR and/or 4.

The amount of additional ceramide ranges from 0.001% to 30%, preferably 0.001% to 10%, and more particularly 0.001% to 5%, relative to the total weight of the lipid composition constituting the vesicles.

The term "ceramide 2.5" is intended to mean a compound, the constitution of which can be represented by the formula (IV) below:

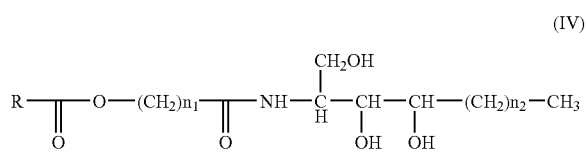

(IV)

in which $n_1$ ranges from 22 to 35, preferably from 25 to 33, more preferably from 26 to 29, and $n_2$ ranges from 11 to 21, preferably from 13 to 17, more preferably from 13 to 15, and RCO denotes a linoleoyl residue. The value of $n_1$ is preferably equal to 29.

The compounds of formula (IV) can be isolated from lipid samples taken by noninvasive methods from normal volunteers. These lipid samples are then subjected to a preparative and analytical treatment for separating and identifying the ceramide families.

Another potential source of the compounds of formula (IV) lies in the use of enzymes such as trans-acylases which act on precursors or modulators of these enzymes.

The precursors are in particular compounds of formula (V) below:

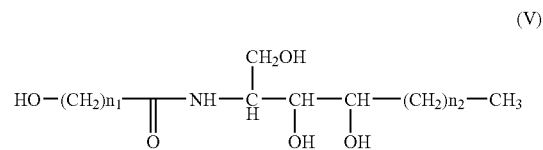

(V)

in which $n_1$ ranges from 22 to 35, preferably from 25 to 33, more preferably from 26 to 29, and $n_2$ ranges from 11 to 21, preferably from 13 to 17, more preferably from 13 to 15.

The value of $n_1$ is preferably equal to 29.

These precursors correspond to the compounds of formula (IV) which have not been esterified on the terminal OH of the hydroxylated fatty acid.

The term "ceramide STAR" is intended to mean a compound the constitution of which can be represented by formula (VI) below:

$$\text{H}_3\text{C}-(\text{CH}_2)_{n_3}-\underset{\underset{\text{OH}}{|}}{\text{CH}}-\underset{\text{O}}{\overset{\overset{\text{CH}_2\text{O}-\overset{\text{O}}{\overset{\|}{\text{C}}}-(\text{CH}_2)_{n_5}-\text{CH}_3}{|}}{|}}-\text{NH}-\underset{\text{H}}{\overset{|}{\text{C}}}-\underset{\underset{\text{OH}}{|}}{\text{CH}}-\text{CH}=\text{CH}-\underset{\underset{\text{OH}}{|}}{\text{CH}}-(\text{CH}_2)_{n_4}-\text{CH}_3 \quad (\text{VI})$$

in which $n_3$ is an integer ranging from 17 to 35, preferably from 21 to 30, preferentially from 23 to 28, more preferably it is equal to 25, 26 or 27, $n_4$ is an integer ranging from 9 to 18, preferably from 11 to 15, preferentially from 11 to 13, more preferably equal to 11, and $n_5$ is an integer ranging from 12 to 18, preferably from 14 to 16, preferably equal to 14.

The compounds of formula (VI) can be isolated from lipid samples taken by noninvasive methods from normal volunteers. These lipid samples are then subjected to a preparative and analytical treatment for separating and identifying the ceramide families.

Another potential source of the compounds of formula (VI) lies in the use of enzymes such as trans-acylases which act on precursors or modulators of these enzymes.

The precursors are in particular compounds of formula (VII) below:

$$\text{H}_3\text{C}-(\text{CH}_2)_{n_3}-\underset{\underset{\text{OH}}{|}}{\text{CH}}-\underset{\text{O}}{\overset{\overset{\text{CH}_2\text{OH}}{|}}{|}}-\text{NH}-\underset{\text{H}}{\overset{|}{\text{C}}}-\underset{\underset{\text{OH}}{|}}{\text{CH}}-\text{CH}=\text{CH}-\underset{\underset{\text{OH}}{|}}{\text{CH}}-(\text{CH}_2)_{n_4}-\text{CH}_3 \quad (\text{VII})$$

in which $n_3$ is an integer ranging from 17 to 35, preferably from 21 to 30, preferentially from 23 to 28, more preferably from 25 to 27, and $n_4$ is an integer ranging from 9 to 18, preferably from 11 to 15, preferentially from 11 to 13, more preferably equal to 11.

These precursors correspond to the compounds of formula (VI) which have not been esterified in the 1-position.

Advantageously, the vesicular dispersion according to the invention may also contain at least one additional active agent.

If the active agents are water-soluble, they are introduced into the encapsulated hydrophilic phase of the vesicles.

If the active agents are lipid-soluble, they are introduced into the lipid phase constituting the membrane.

If the active agents are amphiphilic, they are distributed between the lipid phase and the encapsulated hydrophilic phase with a partition coefficient which varies depending on the nature of the amphiphilic active agent and the respective compositions of the lipid phase and of the encapsulated hydrophilic phase.

As active agents, use may be made of at least one compound chosen from: desquamating agents; moisturizers; depigmenting or propigmenting agents; anti-glycation agents; NO-synthase inhibitors; agents for stimulating the synthesis of dermal or epidermal macromolecules and/or preventing degradation thereof; agents for stimulating fibroblast and/or keratinocyte proliferation or stimulating keratinocyte differentiation; muscle relaxants; tightening agents; anti-pollution agents and/or free-radical scavengers; agents for acting on the microcirculation; agents for acting on the energy metabolism of cells; and mixtures thereof.

Advantageously, the vesicular dispersion according to the invention may also contain at least one other compound for improving the barrier function. This derivative is chosen from ascorbic acid (vitamin C) or analogues thereof, lecithins, glyco-sphingolipids, phospholipids, cholesterol and derivatives thereof, phytosterols (stigmasterol, β-sitosterol, campesterol), essential fatty acids, 1,2-diacylglycerol, 4-chromanone, pentacyclic triterpenes such as ursolic acid, petroleum jelly and lanolin.

Preferably, the compound for improving the barrier function is ascorbic acid in the D or L form, advantageously in the L form, or its analogues chosen from its salts, preferably sodium ascorbate, magnesium ascorbylphosphate or sodium ascorbylphosphate, its esters, preferably its acetic, propionic or palmitic esters, or its sugars, preferably glycosylated ascorbic acid.

In a known manner, the compositions according to the invention may also contain adjuvants which are usual in the cosmetics field, such as preservatives, antioxidants, solvents, fragrances, odor absorbers, neutralizing agents, sunscreens, polymers, emulsifiers and coemulsifiers, and dyestuffs and colorants.

The compositions according to the invention may be introduced into any cosmetic carrier provided in all the pharmaceutical forms conventionally used in the cosmetics field: it may in particular be an optionally gelled aqueous solution, a dispersion of the lotion type, optionally two-phase, an emulsion obtained by dispersion of a fatty phase in an aqueous phase (O/W emulsion) or vice verse (W/O emulsion), or a triple emulsion (W/O/W or O/W/O emulsion). These forms are prepared according to the usual methods. According to this invention, use is preferably made of a cosmetic carrier in the form of an oil-in-water emulsion.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Preparation of the ceramide 7 of formula (I) by TLC from human stratum corneum:

Step 1: Turbine extraction

Starting sample: Epidermis from a normal volunteer

Action: organic solvents (most commonly a 2/3 mixture of hexane/ethanol) are passed through the stratum corneum so as to entrain the lipids, by virtue of a turbine.

Final sample: Epidermal lipids in solvated form.

Step 1a: Extraction using tape stripping

Starting sample: Epidermis from a normal volunteer

Action: an adhesive strip–lacquer+nylon–is applied to the skin of volunteers, and the whole is torn off, entraining, by the same token, part of the stratum. The strips are then placed in the presence of solvents (of the chloroform/methanol (2/1) type, with stirring).

Final sample: Epidermal lipids in solvated form.

Step 2: Isolation of ceramides 7

Starting sample: Epidermal lipids in solvated form (total lipids)

Action: Separation of ceramide families

After concentration, if necessary, of the lipid pool thus obtained (the concentration being obtained by evaporation of part of the solvents), the pool of lipids is deposited on a 20×20 cm Whatman LK5 or Merck 5721 silica plate and 2 successive elutions are carried out with a mixture of chloroform/methanol/acetic acid in the ratio 190/5/1 for the first elution and the ratio 190/9/1 for the second elution.

The classes of ceramides are detected under ultraviolet light (at 254 nm) after spraying the plate with a solution of primuline at 5 mg/100 ml (revelation of the lacquer). This observation makes it possible to delimit about ten contiguous zones on the silica plate, numbered for example from 1 to 10 ranging from the most eluted zone to the least eluted zone. The silica of each of these zones is scraped off, recovered and extracted (so as to extract the ceramides therefrom) several times with a mixture of chloroform/methanol (2/1). The organic phases are pooled and washed with water and then evaporated to dryness so as to obtain the pure ceramide compounds. These ceramides (grouped together therefore by migration bands) are then redissolved in a mixture of chloroform/methanol (2/1). A small proportion of each sample is removed for analytical identification (see structural analysis of the ceramide compounds, paragraph below) in order to determine the major ceramide class and the impurities (generally other ceramides). It is thus possible to identify the sample containing ceramide 7, generally mixed with ceramide 6 (impurity).

Final sample: Solvated ceramide 7 (+ceramide 6 in the form of impurities).

Step 3: Purification of the ceramide 7 sample if necessary

Starting sample: Solvated ceramide 7 (+ceramide 6 in the form of impurities) Action: The sample containing the ceramide 7 is then purified by repeating step 2: deposition of the sample, revelation, scraping off of the silica and extraction of the ceramides, identification of the band comprising mainly ceramide 7 (final structural analysis).

Final sample: Purified ceramide 7 of formula (I).

Structural analysis of the ceramide compounds:

The sample intended for analysis is divided up into two fractions.

A derivation of the first ceramide fraction is carried out using benzoyl chloride. The benzoyl derivatives thus obtained are separated by high performance liquid chromatography and injected into a mass spectrograph at the column outlet by HPLC-MS coupling.

The second fraction undergoes an alkali hydrolysis so as to release the sphingoid bases contained in the ceramides. The released bases are derivatized with ortho-phthaldehyde before being separated by HPLC with detection by fluorescence.

The set of analytical results thus obtained makes it possible to assign a precise molecular structure to each ceramide present in the sample.

EXAMPLE 2

Preparation of ceramide 5.5 by TLC from human stratum corneum:

The preparation of ceramide 5.5 is identical to that of ceramide 7 of Example 1, with the difference that the band isolated after structural analysis of the ceramide content of the various migration bands will be the band containing mainly ceramide 5.5, and with the difference that the latter is generally associated with a greater amount of impurities (ceramides 5) and that obtaining it in a correctly purified form possibly requires repeating purification step 3 one or more times if necessary.

EXAMPLE 3

Evaluation of the effectiveness of the vesicular dispersions according to the invention on the barrier function of reconstructed skin:

The two suspensions below are prepared:
Formula with ceramide 7-free niosomes:

| | |
|---|---|
| Sorbitan palmitate (Span 40 sold by Uniquema) | 0.225% |
| Cholesterol | 0.225% |
| N-stearoyl-L-glutamic acid, disodium salt | 0.050% |
| Propylene glycol | 3.000% |
| Water qs | 100.000% |

Formula with niosomes containing ceramide 7:

| | |
|---|---|
| Sorbitan palmitate | 0.2250% |
| Cholesterol | 0.1250% |
| N-stearoyl-L-glutamic acid, disodium salt | 0.0500% |
| Ceramide 7 | 0.0315% |
| Distilled water qs | 100.0000% |

Procedure:

In the 2 cases, the lipids are combined beforehand in a methanol/chloroform (50/50 by weight) solvent phase. The solvent is then evaporated off under reduced pressure using a rotary evaporator. The lipid film formed on the wall of the round-bottomed flask is then solubilized with an aqueous octylglucoside solution (6%) so as to form octylglucoside/vesicular lipid mixed micelles. This solution is then dialyzed for 24 h against distilled water. The liposomes form as the octylglucoside is dialyzed.

A study is then carried out on three kits of twelve wells, each containing 1 cm$^2$ of EPISKIN™ epidermis.

The various treatments are:
a control kit, i.e., not treated,
a placebo kit, i.e., treated with a formula with ceramide 7-free niosomes,
a kit treated with ceramide 7 formulated in a formula with niosomes (formula CER 7).

The three kits are treated by topical application: for each type of treatment (with the exception of the control kit), two microlitres of formula are applied to the surface of each reconstructed epidermis. The treatment is repeated twice at 48 h intervals. The epidermis are then removed, the surfaces are washed, and the lipids contained in each epidermis are extracted. The sphingo-lipids (essentially ceramides) are, finally, quantified by analyzing their sphingoid base.

Figure 2:
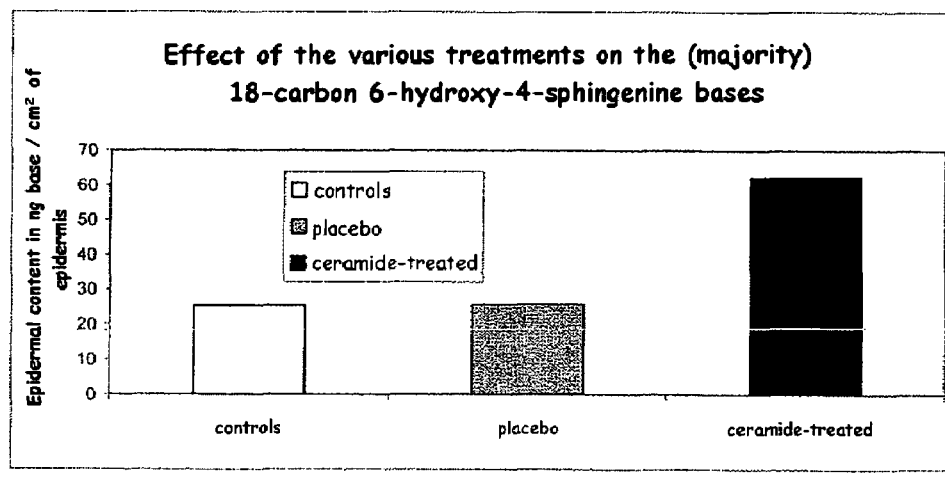

Under the treatment conditions presented above, the results show a substantial increase in 6-hydroxysphingenine bases found in the epidermis of the EPISKIN™ reconstructed skin models treated with the formula with liposomes containing ceramide 7, compared to an untreated epidermis or an epidermis treated with the placebo, as shown in the histogram in FIG. 2.

The formulation of ceramide 7 in a vesicular dispersion which stabilizes it and makes it bioavailable makes it possible to improve the ceramide profile of the reconstructed epidermis of the EPISKIN™ model. Now, increasing the proportion of 6-hydroxy-sphingenine-base ceramides by increasing the proportion of ceramide 7 in the profile of reconstructed skin models such as EPISKIN™ makes it possible to increase the barrier function of the model.

This method therefore, by making the barrier function of the reconstructed skin models more similar to the barrier function of normal human skin, makes it possible to improve said barrier function.

EXAMPLE 4

Effect of the ceramide 7 formulated in a niosome according to the invention on the barrier function of EPISKIN™ reconstructed epidermis Principle of the method of a penetration study: Evaluation of the condition of the barrier function of reconstructed epidermis of the EPISKIN™ model, treated with the ceramide 7 in a niosome formulation by topical application, by means of a study of penetration of radiolabelled caffeine on diffusion cells in static mode: radiolabelled caffeine, which is an amphiphilic molecule, penetrates through the epidermis to a greater or lesser degree depending on the quality of said epidermis; the more the molecule passes through, the more the barrier function is impaired.

The treatments of the reconstructed epidermis of the EPISKIN™ model were carried out between the 8th and 14th day of culturing, by application to the surface of the epidermis of 211 either of the niosome formula containing ceramide 7, or of the ceramide 7-free formula (called placebo formula) as proposed in Example 3.

On the 14th day of culturing, and after stabilization of the models in the diffusion cells, 90 µl (322 µl/cm$^2$) of solution of excess C$^{14}$ caffeine (10 mM in glycerol, 135 µCi/mMol) are applied to the surface of the epidermis. After penetration for 16 h, the excess is removed and recovered. The skin is, in turn, recovered and the tissues are digested. The radioactivity from the medium, then from the skin, and then from the excess are then counted in a scintillation counter.

The total amounts of radioactivity thus recovered are then brought to the same experimental value of deposit in order to standardize the latter and thus to be able to make a better comparison of the effect of the various treatments. In addition, in order to have a result which was as representative of the study as possible, the following values were paired: surface excess+washes (since the washes constitute everything which is above the epidermis), firstly, and recipient medium+tissue (since everything which could be found in the tissue has therefore penetrated through).

Figure 3:
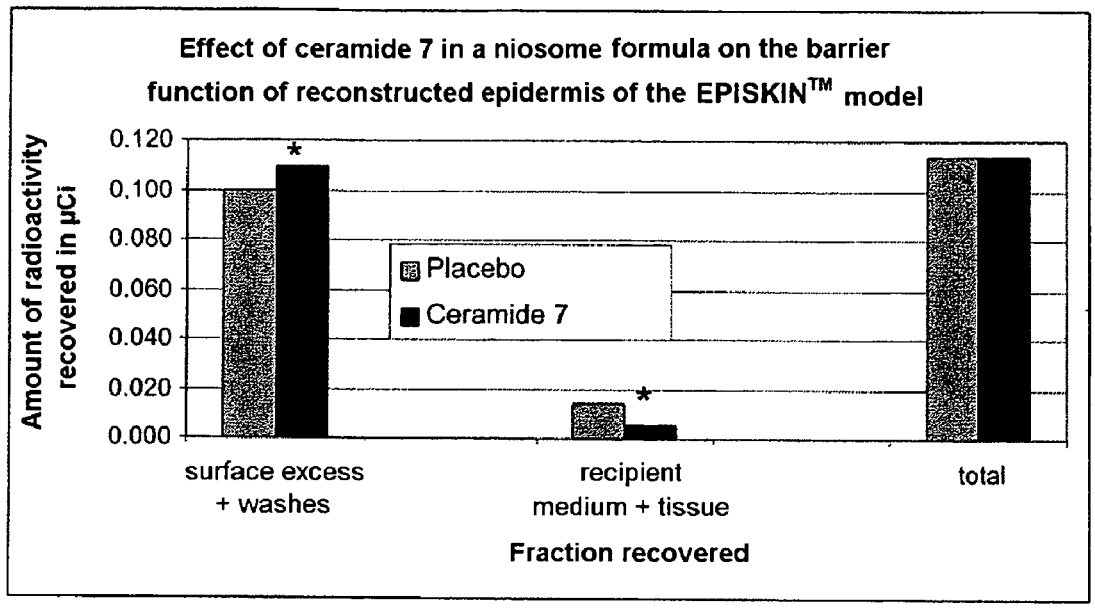

The results of this study are given in the histogram in FIG. 3.

The histogram in FIG. 3 shows an improved barrier function for the reconstructed skin of the EPISKIN™ model after treatment with ceramide 7 formulated in niosomes, since less caffeine has penetrated into the tissues and more has remained at the surface.

EXAMPLE 5

Demonstration of the deficiency in 6-hydroxy-4-sphingenine-base ceramides in dry skin:

In this study, the lipid profiles of samples of normal skin (dryness score 0) and dry skin (dryness score 2) were compared. The samples (lipids directly extracted, by means of a turbine, with solvents crossing the stratum) are taken from 22 individuals with a score of 0 and 19 individuals with a score of 2. The samples were then pooled by score for reasons of analytical sensitivity.

The ceramides were therefore identified by HPLC/mass spectrometry detection after separation of the various classes by thin layer chromatography. A quantification of the ceramides contained in each migration band was then carried out by HPLC/fluorimetric detection, after hydrolysis of the ceramides to bases and fatty acids and specific derivation of the bases (very precise quantitative approach).

Figure 4:
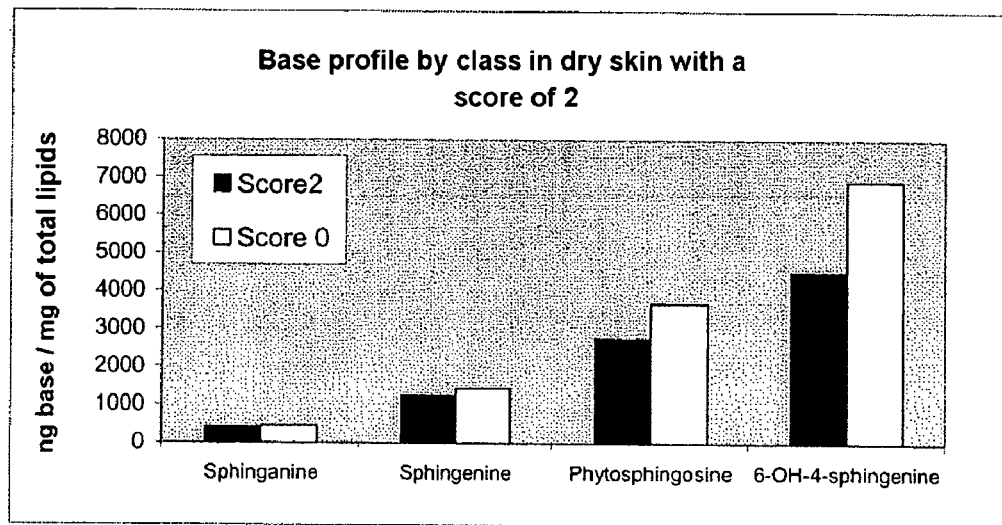

The results are given in FIG. 4.

This study therefore shows that the average amount of 6-hydroxy-4-sphingenine-base ceramides (CER 5.5, 7 and 4) is less in dry skin with a score of 2 compared to normal skin with a score of 0.

EXAMPLE 6

Preparation of ceramide STAR:

Lipid sample:

The samples are taken from a group of 22 women (normal volunteers) with an average age of 33.8±8.8, whose skin is described as normal by clinicians. The samples are taken from the forearm using a turbine after cleaning of the skin with cotton wool soaked in ether in order to remove traces of sebum. The extraction chamber of the turbine, filled with 10 ml of a mixture of hexane/ethanol (2/3) is applied over a surface area of 12.56 cm$^2$. The mixture is agitated for 1 minute and is then collected using a glass syringe and then stored in a glass container at −20° C.

Three samples are thus taken from the forearm of each individual. The samples are then pooled, evaporated to dryness using a rotary evaporator, taken up in 1 ml of chloroform/methanol (2/1) and stored at −20° C. The solids content corresponding to all these samples is 36.4 mg and represents an extracted surface area of 829 cm$^2$.

Separation and isolation of the ceramides:

In a first step, the ceramides are separated from the other categories of lipids by depositing the lipid sample obtained above on a normal-phase silica cartridge (silica gel 60). After removal of the neutral lipids with 10 ml of chloroform containing 1% acetic acid, the ceramides are eluted with 10 ml of a mixture of chloroform/methanol (95/5). The ceramides are then stored in 1 ml of chloroform at −20° C.

In a second step, the various ceramides are separated by thin layer chromatography under the following conditions:

1.7 mg of the mixture of ceramides obtained at the end of the first step are deposited on a Whatman LK5 20×20 cm silica plate and 2 successive elutions are carried out with a mixture of chloroform/methanol/acetic acid in the ratio 190/5/1 for the first elution and the ratio 190/9/1 for the second elution.

The ceramide classes are detected under ultraviolet light (at 254 nm) after spraying the plate with a solution of primuline at 5 mg/100 ml. This observation makes it possible to delimit 10 contiguous zones on the silica plate, numbered from 1 to 10 ranging from the most eluted zone to the least eluted zone. The silica of each of these zones is scraped off, recovered, and extracted several times with a mixture of chloroform/methanol (2/1). The organic phases are pooled and washed with water, and then evaporated to dryness so as to obtain pure ceramide compounds. A portion of these ceramides is then redissolved in a mixture of chloroform/methanol (2/1) for analytical identification.

The ceramides described above such that n3 is from 17 to 35, n4 is from 9 to 18, and n5 is from 12 to 18, are recovered in spot No. 1 on the silica plate.

Structural analysis of the ceramide compounds:

The sample intended for analysis is divided up into two fractions.

A derivation of the first ceramide fraction is carried out using benzoyl chloride. The benzoyl derivatives thus obtained are separated by high performance liquid chromatography and injected into a mass spectrograph at the column outlet by HPLC-MS coupling.

The second fraction undergoes an alkali hydrolysis so as to release the sphingoid bases contained in the ceramides. The released bases are derivatized with ortho-phthaldehyde before being separated by HPLC with detection by fluorescence.

The set of analytical results thus obtained makes it possible to assign a precise molecular structure to each ceramide present in the sample.

A fraction A containing the ceramides such that $n_3$ is from 25 to 27, n is equal to 11, and $n_5$ is equal to 14 is isolated from the mixture.

EXAMPLE 7

Preparation of ceramide 2.5:

The preparation of ceramide 2.5 is identical to that of the ceramide STAR of Example 6, with the exception of the step for separating and isolating the ceramides, at the end of which the ceramides described above such that $n_1$ is from 22 to 35, and $n_2$ is from 11 to 21, and RCO denotes a linoleoyl residue, are recovered in spot No. 4 on the silica plate. In addition, during the structural analysis of the ceramide compounds, a fraction A containing the ceramides such that $n_1$ is equal to 29 and $n_2$ is from 13 to 15 is isolated from the mixture.

EXAMPLE 8

Culture Medium to Which a Derivative of the Ceramide 7 family in Combination with BSA may be added:

| | |
|---|---|
| DMEM (3 volumes) and HAM F12 (1 volume) culture media sold by DULBECCO and GIBCO | 450 ml |
| Iron-supplemented calf serum | 50 ml |
| EGF (epidermal growth factor) (10 ng/ml) | 500 µl |
| Isoproterenol ($10^{-6}$M) | 500 µl |
| Hydrocortisone (0.4 µg/ml) | 400 µl |
| L-Glutamine (2 mM) | 5 ml |
| DL-α-tocopherol acetate | 10.6 µmol |
| L-carnitine | 5.1 µmol |
| BSA (bovine serum albumin) | 12.1 µmol |
| Ceramide 7 | 175 µg (0.25 µmol) |

EXAMPLE 9

Compositions:
Formula with liposomes containing ceramide 7:

| | |
|---|---|
| Soybean lecithin (enriched with 75% of phosphatidylcholine) sold by SEPPIC under the trademark Lipoïd S75 | 0.5000% |
| Propylene glycol | 3.0000% |
| Ceramide 7 | 0.0315% |
| Water qs | 100.0000% |

Formula with liposomes containing ceramide 5.5:

| | |
|---|---|
| Soybean lecithin (enriched with 75% of PC) lipoïd S75 | 0.5000% |
| Propylene glycol | 3.0000% |
| Ceramide 5.5 | 0.0315% |
| Water qs | 100% |

Moisturizing cream based on a suspension of ceramide 7:
Vesicular phase:

| | |
|---|---|
| Sorbitan palmitate | 2.250% |
| Cholesterol | 1.125% |
| N-stearoyl-L-glutamic acid, disodium salt | 0.500% |
| Ceramide 7 | 0.315% |
| Glycerol | 5.000% |
| Methylparaben | 0.300% |
| Demineralized water qs | 100% |

A1 phase:

| | |
|---|---|
| Stearyl heptanoate | 4.0% |
| Codex petroleum jelly | 1.5% |
| Avocado oil | 3.2% |
| Jojoba oil | 3.0% |
| Volatile silicone oil | 2.7% |
| Vitamin E acetate | 1.0% |
| Natural D-α-tocopherol sold by Henkel under the name "COPHEROL 1300" | 1% |
| Vitamin F glycerides | 3% |

A2 phase:

| | |
|---|---|
| Silicone gum sold by Dow Corning under the name "Q2-1403 FLUID" | 3.0% |
| Propylparaben | 0.2% |
| Fragrance | 0.3% |

B phase:

| | |
|---|---|
| Mixture of carboxyvinyl polymers sold under the name "CARBOPOL 940" by Goodrich | 0.40% |
| Demineralized water | 9.50% |
| Triethanolamine | 0.25% |

The vesicular phase is prepared according to one of the methods already described and is then homogenized by being passed 2 times through a high-pressure homogenizer, at 500 b, of the Soavi OBL 20 or Microfluidics type.

The A1 and A2 phases are then added, with sufficient rotor-stator stirring to produce a sufficiently stable predispersion of oil. The entire mixture is then homogenized twice at 500 b.

The B phase, prepared beforehand, is added to the emulsion prepared above and dispersed using a deflocculating turbine.

A smooth white cream suitable for treating dry skin is obtained.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for preparing a reconstructed epidermis/skin equivalent from a culture medium therefor and supplemented with at least one ceramide 7 and/or 5.5 compound, comprising introducing said at least one ceramide 7 and/or 5.5 compound into the culture medium of said reconstructed epidermis/skin equivalent and/or topically applying onto the face surface of said reconstructed epidermis/skin equivalent a composition which comprises lipid lamellar vesicles incorporating at least one ceramide 7 and/or 5.5 compound.

2. The method as defined by claim 1, said at least one ceramide 7 and/or 5.5 compound having the following structural formula (I):

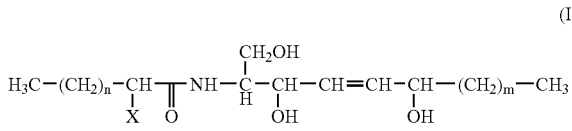

in which X is a hydrogen atom or a hydroxyl group; n is an integer ranging from 19 to 29, and m is an integer ranging from 9 to 19.

3. The method as defined by claim 2, wherein formula (I), n ranges from 21 to 27 and m ranges from 9 to 15.

4. The method as defined by claim 3, wherein formula (I), n is 21, 22 or 23 and m 11, 12 or 13.

5. The method as defined by claim 4, wherein formula (I), n is 21 and m is 11.

6. The method as defined by claim 2, wherein formula (I), X is a hydroxyl group.

7. The method as defined by claim 2, wherein formula (I), X is a hydrogen atom.

8. The method as defined by claim 1, said at least one ceramide 7 and/or 5.5 compound being dissolved in a solvent when introduced into the culture medium.

9. The method as defined by claim 8, said solvent comprising ethanol or DMSO, the final ratio of solvent introduced into the culture medium not exceeding 1/1,000.

10. The method as defined by claim 1, comprising introducing into the culture medium a combination which comprises said at least one ceramide 7 and/or 5.5 compound and at least one molecule capable of transporting said at least one ceramide compound and rendering it or them bioavailable within the reconstructed epidermis/skin equivalent from said culture medium.

11. The method as defined by claim 10, said at least one molecule capable of transporting said at least one ceramide compound comprising BSA and/or a cyclodextrin.

12. The method as defined by claim 11, said at least one molecule capable of transporting said at least one ceramide compound comprising BSA, introduced into said culture medium in an amount less than or equal to 100 μmol/l.

13. The method as defined by claim 10, said combination also comprising at least one antioxidant and at least one cellular transporter, introduced into said culture medium in amounts of less than or equal to 50 μmol/l and 100 μmol/l, respectively.

14. The method as defined by claim 13, said at least one antioxidant comprising DL-α-tocopherol and said at least one cellular transporter comprising L-carnitine.

15. The method as defined by claim 2, comprising introducing into said culture medium lipid lamellar vesicles incorporating at least one ceramide 7 and/or 5.5 compound having the formula (I).

16. The method as defined by claim 2, comprising introducing into said culture medium from 10 g/l to $10^{-6}$ g/l of said at least one compound of formula (I).

17. The method as defined by claim 2, comprising topically applying onto the face surface of said reconstructed epidermis/skin equivalent a composition which comprises lipid lamellar vesicles incorporating at least one ceramide 7 and/or 5.5 compound of formula (I).

18. A composition of matter comprising a dispersion, in an external aqueous phase, of vesicles which comprise lipid lamellar phases separated from each other by hydrophilic layers, said lamellar phases comprising at least one amphiphilic lipid and at least one ceramide 7 and/or 5.5 compound having the following structural formula (I):

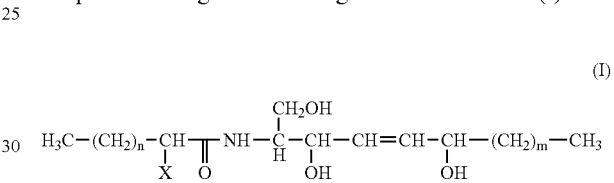

in which X is a hydrogen atom or a hydroxyl group; n is an integer ranging from 19 to 29, and m is an integer ranging from 9 to 19.

19. The composition as defined by claim 18, said vesicles comprising niosomes or liposomes.

20. The composition as defined by claim 18, said at least one ceramide 7 and/or 5.5 compound of formula (I) comprising from 0.001% to 30% by weight of the lipid composition constituting the vesicles.

21. The composition as defined by claim 18, said at least one ceramide 7 and/or 5.5 compound of formula (I) comprising from 0.001% to 10% by weight of the lipid composition constituting the vesicles.

22. The composition as defined by claim 18, said at least one ceramide 7 and/or 5.5 compound of formula (I) comprising from 0.001% to 5% by weight of the lipid composition constituting the vesicles.

23. The composition as defined by claim 18, the weight ratio of the amount of lipid phase to the amount of aqueous phase in the dispersion ranging from 1/1,000 to 300/1,000.

24. The composition as defined by claim 18, said lamellar phases comprising at least one amphiphilic lipid being selected from the group consisting of the esters and/or the ethers of a polyol and of a fatty acid, whether or not polyoxyethylenated; the esters and/or the ethers of a fatty acid of an α-butylglycoside; and synthetic or natural phospholipids, whether or not hydrogenated.

25. The composition as defined by claim 24, said lamellar phases comprising at least one amphiphilic lipid being selected from the group consisting of mixtures of esters and/or mixtures of ethers of at least one polyol selected from the group consisting of a polyethylene glycol having from 1 to 60 ethylene oxide units, sorbitan, sorbitan bearing 2 to 60 ethylene oxide units, glycerol bearing 2 to 30 ethylene oxide units, polyglycerols having 2 to 15 glycerol units, sucroses, and glucoses bearing 2 to 30 ethylene oxide units, and at least one fatty acid comprising a linear or branched, saturated or unsaturated $C_5$–$C_{22}$ alkyl radical, the number of alkyl radicals per polyol group ranging from 1 to 10.

26. The composition as defined by claim 24, said lamellar phases comprising at least one amphiphilic lipid being selected from the group consisting of mixtures of esters and/or mixtures of ethers of various fatty acids of an α-butylglucoside, the various fatty chains of which comprise, with respect to one another, a similar number of carbon atoms, or mixtures of mono-, di-, tri- or polyesters and/or mixtures of mono-, di-, tri- or polyethers of the same fatty acid of an α-butylglucoside; said esters and said ethers of a fatty acid of an α-butylglucoside comprising a fatty chain having from 8 to 24 carbon atoms.

27. The composition as defined by claim 18, said lamellar phases also comprising at least one ionic amphiphilic lipid.

28. The composition as defined by claim 27, said at least one ionic amphiphilic lipid being selected from the group consisting of:

alkali salts of dicetyl and dimyristyl phosphate;

alkali salts of cholesterol sulphate;

alkali salts of cholesterol phosphate;

lipoamino acids and salts thereof, monosodium and disodium acylglutamates, the disodium salt of N-stearoyl-L-glutamic acid;

sodium salts of phosphatidic acid;

phospholipids;

alkylsulphonic compounds of formula (X):

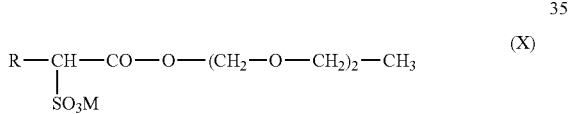

in which R is a $C_{16}$–$C_{22}$ alkyl radical and M is an alkali or alkaline earth metal, and mixtures thereof;

quaternary ammonium salts, and fatty amines and salts thereof.

29. The composition as defined by claim 28, said at least one ionic amphiphilic lipid comprising a quaternary ammonium salt selected from the group consisting of:

quaternary ammonium salts having the following formula (XI):

in which the radicals $R_1$ to $R_4$, which may be identical or different, are each a linear or branched aliphatic radical having from 1 to 30 carbon atoms, or an aromatic radical; and X is an anion selected from the group consisting of halides, phosphates, acetates, lactates, ($C_2$–$C_6$)alkyl sulphates, alkyl sulphonates and alkylaryl sulphonates;

quaternary ammonium salts of imidazolinium having the following formula (XII):

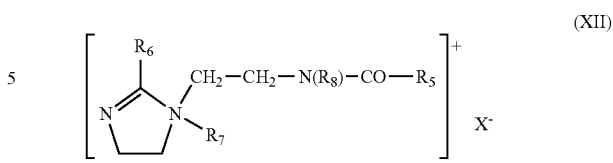

in which $R_5$ is an alkenyl or alkyl radical having from 8 to 30 carbon atoms; $R_6$ is a hydrogen atom, a $C_1$–$C_4$ alkyl radical or an alkenyl or alkyl radical having from 8 to 30 carbon atoms; $R_7$ is a $C_1$–$C_4$ alkyl radical; $R_8$ is a hydrogen atom or a $C_1$–$C_4$ alkyl radical; and X is an anion selected from the group consisting of halides, phosphates, acetates, lactates, alkyl sulphates, alkyl sulphonates and alkylaryl sulphonates;

diquaternary ammonium salts having the following formula (XIII):

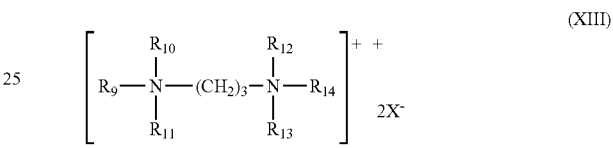

in which $R_9$ is an aliphatic radical having approximately 16 to 30 carbon atoms;

$R_{10}$, $R_{11}$, $R_{12}$, $R_{13}$ and $R_{14}$, which may be identical or different, are each hydrogen or an alkyl radical having from 1 to 4 carbon atoms; and X is an anion selected from the group consisting of halides, acetates, phosphates, nitrates and methyl sulphates; and quaternary ammonium salts comprising at least one ester function.

30. The composition as defined by claim 29, said at least one ionic amphiphilic lipid comprising a quaternary ammonium salt containing at least one ester function and having the following formula (XIV):

$$R_{17}-\overset{O}{\overset{\|}{C}}-(OC_nH_{2n})_y-\overset{(C_rH_{2r}O)_z-R_{18}}{\overset{|}{N^+}}-(C_pH_{2p}O)_x-R_{16} \ , \ X^-$$
$$\underset{R_{15}}{|}$$

in which $R_{15}$ is a $C_1$–$C_6$ alkyl radical or a $C_1$–$C_6$ hydroxyalkyl or dihydroxyalkyl radical; $R_{16}$ is the radical $R_{19}$—CO—, a linear or branched, saturated or unsaturated $C_1$–$C_{22}$ hydrocarbon-based radical $R_{20}$, or a hydrogen atom; $R_{18}$ is a hydrogen atom, the radical $R_2'$—CO—, or a linear or branched, saturated or unsaturated $C_1$–$C_6$ hydrocarbon-based radical $R_{22}$; $R_{17}$, $R_{19}$ and $R_{21}$, which may be identical or different, are each a linear or branched, saturated or unsaturated $C_7$–$C_2$, hydrocarbon-based radical; n, p and r, which may be identical or different, are each integers ranging from 2 to 6; y is an integer ranging from 1 to 10; x and z, which may be identical or different, are each integers ranging from 0 to 10; and $X^-$ is a simple or complex, organic or mineral anion; with the proviso that the sum x+y+z ranges from 1 to 15, that, when x is 0, then $R_{16}$ is $R_{20}$, and that, when z is 0, then $R_{18}$ is $R_{22}$.

31. The composition as defined by claim 30, wherein formula (XIV), $R_{15}$ is a methyl or ethyl radical; x and y are equal to 1; z is equal to 0 or 1; n, p and r are equal to 2; $R_{16}$ is the radical $R_{19}$—CO—, a methyl, ethyl or $C_{14}$–$C_{22}$ hydrocarbon-based radical, or a hydrogen atom; $R_{18}$ is the radical $R_{21}$—CO—, or a hydrogen atom; and $R_{17}$, $R_{19}$ and $R_{21}$, which may be identical or different, are each a linear or branched, saturated or unsaturated $C_3$–$C_{17}$ hydrocarbon-based radical.

32. The composition as defined by claim 27, the weight ratio of the amount of said at least one nonionic amphiphilic lipid to the amount of said at least one amphiphilic lipid ranging from 50/1 to 50/25.

33. The composition as defined by claim 18, said lamellar phases comprising at least one additive selected from the group consisting of sterols, fatty-chain alcohols and diols, and fatty-chain amines and the quaternary ammonium derivatives thereof.

34. The composition as defined by claim 33, said at least one additive comprising cholesterol.

35. The composition as defined by claim 18, said lamellar phases further comprising at least one ceramide STAR, 1, 2, 2.5, 3, 4, 5 and/or 6.

36. The composition as defined by claim 35, said lamellar phases further comprising the ceramides STAR and/or 4.

37. The composition as defined by claim 18, further comprising at least one other compound for improving the barrier function selected from the group consisting of ascorbic acid or analogues thereof, lecithins, glycosphingolipids, phospholipids, cholesterol and derivatives thereof, phytosterols (stigmasterol, β-sitosterol, campesterol), essential fatty acids, 1,2-diacylglycerol, 4-chromanone, pentacyclic triterpenes, ursolic acid, petroleum jelly, lanolin and mixtures thereof.

38. The composition as defined by claim 18, further comprising at least one other bioactive agent selected from the group consisting of desquamating agents; moisturizers; depigmenting or propigmenting agents; anti-glycation agents; NO-synthase inhibitors; agents for stimulating the synthesis of dermal or epidermal macromolecules and/or preventing degradation thereof; agents for stimulating fibroblast and/or keratinocyte proliferation or stimulating keratinocyte differentiation; muscle relaxants; tightening agents; anti-pollution agents and/or free-radical scavengers; agents for acting on the microcirculation; agents for acting on the energy metabolism of cells; and mixtures thereof.

39. The composition as defined by claim 18, further comprising at least one adjuvant selected from the group consisting of preservatives, antioxidants, solvents, fragrances, odor absorbers, neutralizing agents, sunscreens, polymers, emulsifiers and coemulsifiers, dyestuffs, and mixtures thereof.

40. A regime or regimen for reinforcing the barrier function of normal human epidermis, and/or improving the barrier function of an epidermis exhibiting a deficiency in 6-hydroxy-4-sphingenine-base ceramides, including that of dry skin, or of rough and/or damaged and/or aged and/or sensitive skin, and/or re-establishing or maintaining the integrity of the stratum corneum, and/or improving the surface appearance and/or the moisturization of the skin, and/or improving and/or maintaining the lipid content of human epidermis, comprising topically applying thereon a thus-effective amount of a composition of matter comprising a dispersion, in an external aqueous phase, of vesicles which comprise lipid lamellar phases separated from each other by hydrophilic layers, said lamellar phases comprising at least one amphiphilic lipid and at least one ceramide 7 and/or 5.5 compound having the following structural formula (I):

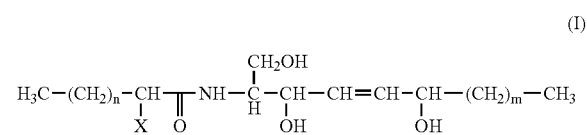

in which X is a hydrogen atom or a hydroxyl group; n is an integer ranging from 19 to 29, and m is an integer ranging from 9 to 19.

41. A regime or regimen for the treatment of atopic skin, comprising topically applying thereon a thus-effective amount of a composition of matter comprising a dispersion, in an external aqueous phase, of vesicles which comprise lipid lamellar phases separated from each other by hydrophilic layers, said lamellar phases comprising at least one amphiphilic lipid and at least one ceramide 7 and/or 5.5 compound having the following structural formula (I):

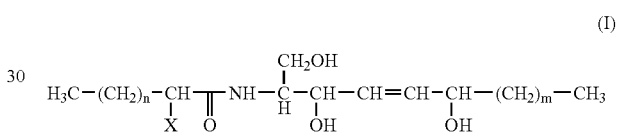

in which X is a hydrogen atom or a hydroxyl group; n is an integer ranging from 19 to 29, and m is an integer ranging from 9 to 19.

42. A regime or regimen for rendering human skin more attractive or moisturizing same, comprising topically applying thereon a thus-effective amount of a composition of matter comprising a dispersion, in an external aqueous phase, of vesicles which comprise lipid lamellar phases separated from each other by hydrophilic layers, said lamellar phases comprising at least one amphiphilic lipid and at least one ceramide 7 and/or 5.5 compound having the following structural formula (I):

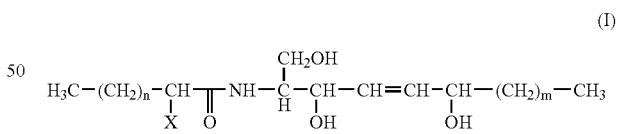

in which X is a hydrogen atom or a hydroxyl group; n is an integer ranging from 19 to 29, and m is an integer ranging from 9 to 19.

43. The method as defined by claim 17, the amount of composition topically applied onto the face surface of the epidermis in culture ranging from 0.5 µl to 10 µl per $cm^2$ of reconstructed epidermal surface.

* * * * *